United States Patent

Isogai et al.

[11] Patent Number: 5,905,562
[45] Date of Patent: May 18, 1999

[54] OPHTHALMIC APPARATUS FOR MEASURING AN EYE TO BE EXAMINED

[75] Inventors: Naoki Isogai, Nishio; Noriji Kawai, Gamagori, both of Japan

[73] Assignee: Nidek Co., Ltd., Gamagori, Japan

[21] Appl. No.: 08/896,608

[22] Filed: Jul. 18, 1997

[30] Foreign Application Priority Data

Jul. 31, 1996 [JP] Japan .................................. 8-219184
Jul. 31, 1996 [JP] Japan .................................. 8-219185

[51] Int. Cl.$^6$ ........................................................ A61B 3/14
[52] U.S. Cl. ........................................... 351/208; 351/205
[58] Field of Search .................................. 351/205, 206, 351/208, 210, 211

[56] References Cited

U.S. PATENT DOCUMENTS

| | | | |
|---|---|---|---|
| 5,406,076 | 4/1995 | Mimura et al. | 250/229 |
| 5,463,430 | 10/1995 | Isogai et al. | 351/208 |
| 5,644,375 | 7/1997 | Suzuki | 351/208 |
| 5,696,573 | 12/1997 | Miwa | 351/208 |

FOREIGN PATENT DOCUMENTS

| | | |
|---|---|---|
| A-6-7292 | 1/1994 | Japan . |
| A-6-46999 | 2/1994 | Japan . |
| A-8-107881 | 4/1996 | Japan . |

*Primary Examiner*—Huy Mai
*Attorney, Agent, or Firm*—Oliff & Berridge, PLC

[57] ABSTRACT

In an ophthalmic apparatus for measuring an eye to be examined, an picture image photographed by a TV camera is processed by image processing circuit, and a position of alignment target image is detected so as to detect an alignment condition of measuring unit opposite to the eye to be examined. The suitability of the alignment condition is judged by a microcomputer, and when it is judged that the alignment condition is proper, a trigger signal is generated so as to start a measurement. Upon the measurement or after the measurement is completed, in case that the alignment condition is detected, the suitability of the alignment condition is judged, and it is judged that the alignment condition deviates from a predetermined allowable condition, a measured result which is obtained by a measurement performance is cancelled, or the measured result is corrected based on a detected result by an alignment detection. The apparatus continues the measurement by generating the trigger signal based on the suitable judged result of the alignment condition until the measured results of predetermined times are obtained, and when the measured results of predetermined times are obtained, a generation of trigger signal is stopped, so that it is monitored whether an alignment target image is not detected within a predetermined period. By this monitoring, when the target is not detected within the predetermined period, it is cancelled that the trigger signal is stopped generating.

11 Claims, 7 Drawing Sheets

$\frac{b}{a} > S$

FIG. 9B $\frac{b}{a} < S$

FIG. 9C $\frac{b}{a} = S$

OPHTHALMIC APPARATUS FOR MEASURING AN EYE TO BE EXAMINED

BACKGROUND OF THE INVENTION

1. Field of the Invention

The present invention relates to an ophthalmic apparatus, and more particularly to the ophthalmic apparatus for starting measurement by positioning the apparatus at a predetermined positional relation to an eye to be examined.

2. Description of Related Art

Regarding ophthalmic apparatuses such as an ophthalmic apparatus for measuring a refractive power of an eye to be examined or an ophthalmic apparatus for measuring a corneal curvature, after an alignment adjustment of measurement optical system of the apparatus to the eye is performed, a trigger signal for starting measurement is inputted so as to start measurement. Further, another apparatus has been proposed such as it provides a detecting mechanism for detecting an alignment condition, also measurement is to be started by automatically generating trigger signal when it is judged that an alignment condition is under a predetermined condition level.

Incidentally, another ophthalmic apparatus such as an ophthalmic apparatus for measuring a refractive power of an eye have a disadvantage that some alignment displacement can be caused during measurement, because it takes times to complete measurement after the trigger signal is generated, and therefore it may be possible that an apparatus will be shifted or the eye will be moved unexpectedly. In this case, such an obtained measured result tends to be improper. However, since there may be another case that an operator cannot realize that alignment displacement has been caused during measurement, it resulted in another disadvantage that some improper measured result were selected.

Generally, a plural measurements of the same eye are repeated in order to take process for obtaining its average value or central value as a measured result. Therefore, in case of an apparatus having means for automatically starting measurement, a continuous measurement has to be carried out until predetermined measurement times are achieved. Among these sort of ophthalmic apparatuses, it has been proposed that an apparatus comprises a TV monitor for observation to display which direction the apparatus should be shifted.

However, in case that such a continues measurement is performed for measurements of predetermined times, it may result in another disadvantage that a switch for separately starting measurement should be pressed, if it is necessary for the same eye to be measured once again after the continues measurement is completed. Although it has been set that measurement can be started automatically, the apparatus used to be necessary to equip with an optional switch for starting measurement. As a switch for starting measurement, the apparatus is generally equipped with a joystick in order to shift an apparatus opposite to an eye to be examined by the operator, but connecting of the joystick with electrical wire may cause some troubles such as break.

In addition, alignment adjustment has a following disadvantage. It had been much desirable to distinguish a direction indication that the apparatus should be moved by handling the joystick during alignment adjustment, especially for even operators who do not accustom himself to use an apparatus, the apparatus may be desirable to distinguish a directional indication that the apparatus should be shifted by handling the joystick.

SUMMARY OF THE INVENTION

The present invention has been made in view of the above circumstances and has an object to overcome the above problem and to provide an ophthalmic apparatus for measuring an eye to be examined, capable of obtaining a high reliable measured result.

The present invention has another object to provide the ophthalmic apparatus for automatically starting measurement without any switching operation after measurements of the predetermined times are completed.

Further, the present invention has another object to provide the ophthalmic apparatus for reducing any production cost for display that it is easy for operator to distinguish directional indications that the apparatus should be moved.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus for measuring an eye to be examined of this invention comprises alignment detecting means for detecting an alignment condition of a measuring means corresponding to the eye to be examined, alignment judging means for judging whether the alignment condition is possible to measure based on a detected result by the alignment detecting means, trigger signal generating means for generating a trigger signal for starting measurement, and measured result judging means for judging that a measured result is error when the alignment judging means judges that the alignment condition after starting measurement deviates from a predetermined allowable standard based on the detected result by the alignment detecting means during measurement or when measurement is completed.

According to the present invention, the ophthalmic apparatus enables to avoid from selecting some improper measured result caused by failure of alignment after measurement is started.

In another aspect of the present invention, the ophthalmic apparatus comprises target projecting means for projecting an alignment target onto the eye to be examined, target detecting means for detecting a target image formed by the target projecting means, alignment judging means for judging whether an alignment condition is possible to measure based on a detected result by the target detecting means, trigger signal generating-controlling means for generating a trigger signal for starting measurement based on a judged result by the alignment judging means, stop means for stopping the trigger signal from being generated whenever a desired measured result is obtained, monitoring means for monitoring whether the target image is detected within a predetermined period by the target detecting means when the trigger signal is stopped from being generated by the stop means, and cancel means for cancelling a stop of generation of the trigger signal when the monitoring means monitors that the target image is not detected within the predetermined period by the target detecting.

Also, according to the present invention, the apparatus enables to automatically start measurement without any switching operations after measurements of predetermined times are completed.

Beside, the apparatus enables to achieve readable directional indications that the apparatus should be moved and enables to reduce a product cost for display.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

In the drawings.

DETAILED DESCRIPTION OF THE PREFERRED EMBODIMENTS

Figure 1:
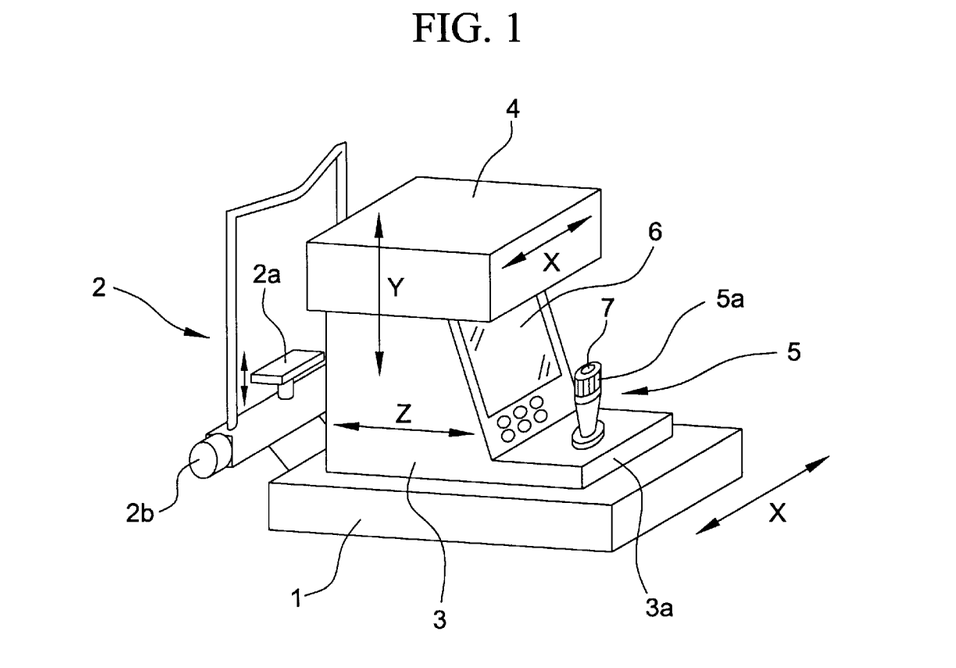
FIG. 1 is a view showing an outline diagram of outward shape of the preferred embodiment of the present invention.

A detailed description of an ophthalmic apparatus for measuring an eye to be examined embodying the present invention will now be given referring to the accompanying drawings. FIG. 1 is a view showing a outline diagram of outward shape of the preferred embodiment. Reference numeral 1 denotes a base on which a face support unit 2 is fixed in order to support an examinee's face. A chin support member 2a is supported on the face support unit 2 so as to be movable up and down. By turning a knob 2b, the chin support member 2a can be moved up and down and a height position of the eye also can be adjusted.

Reference numeral 3 is a body unit, and 4 is a measuring unit having an optical system which will be described hereinafter. Reference number 5 is a joystick for shifting the body unit 3 and the measuring unit 4. By handling the joystick 5, the body unit 3 is slide toward and away (in Z direction) and left and right (in X direction) on horizontal plane. Further, by handling a rotating knob 5a with which the joystick 5 is equipped, the measuring unit 4 is moved up and down (in Y direction) opposite to the body unit 3.

Figure 2:
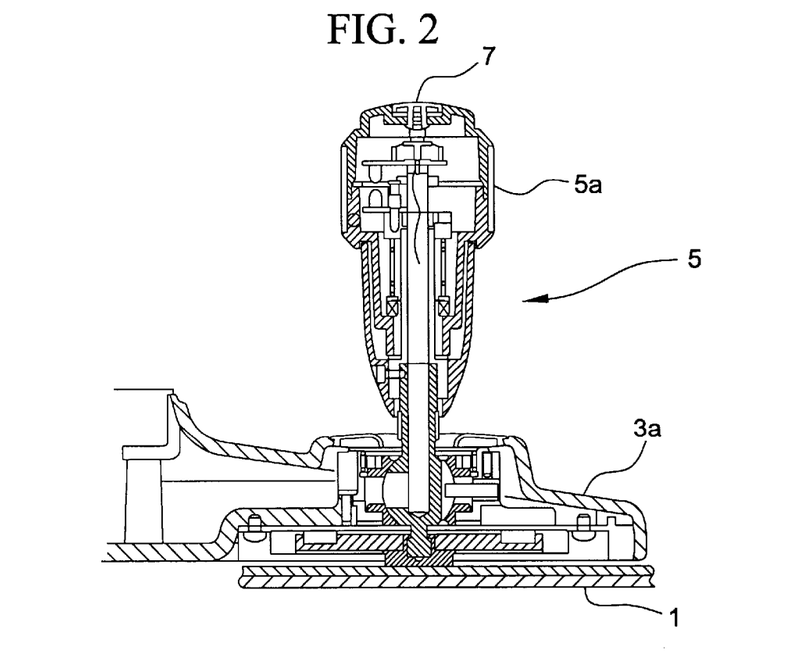
FIG. 2 is a view showing a joystick mechanism shown in FIG. 1.

On shifting of the body unit 3 opposite to the base table 1, a spherical part and bottom part which are formed under a shaft of the joystick 5, a sliding plate for sliding by the bottom part, a friction plate which is touched to the sliding plate and attached to the base 1, and a spherical bearing within a housing 3a which is connected with the body unit 3 are constituted so as to achieve an oscillation of a horizontal direction (as shown in FIG. 2). In addition, regards as up-down shifting of the measuring unit 4 opposite to the body unit 3, by a constitution of a rotating knob 5a on the peripheral top part of the joystick 5, a slit-plate which is rotated with the rotating knob 5a, and a light source and a photodetector which put the slit-plate between them and is provided for the shaft, a rotating direction and an amount of rotation of the rotating knob 5a are detected by a signal of the photodetector, thereby based on the detected result, the driving motor of Y-direction shifting mechanism which shifts the measuring unit 4 in the up-down direction is driven and controlled. The detail of the joystick mechanism is described in Japanese Patent Laid-open No. 6-7292 by the present applicant corresponding to U.S. Pat. No. 5,406,076 ("JOYSTICK MECHANISM FOR OPHTHALMIC APPARATUS") granted to the applicant of the present patent application.

The measuring unit 4 is movable in the left-right and up-down directions opposite to the body unit 3 for automatic alignment. The shifting of left-right direction is led to by X-direction shifting mechanism which is constituted by such a slid mechanism, and the like motor described hereafter.

Reference numeral 6 is a TV monitor for displaying an eye image or information in order to inform an operator. Reference numeral 7 is a measuring start switch provided at the top part of the joystick 5.

Figure 3:
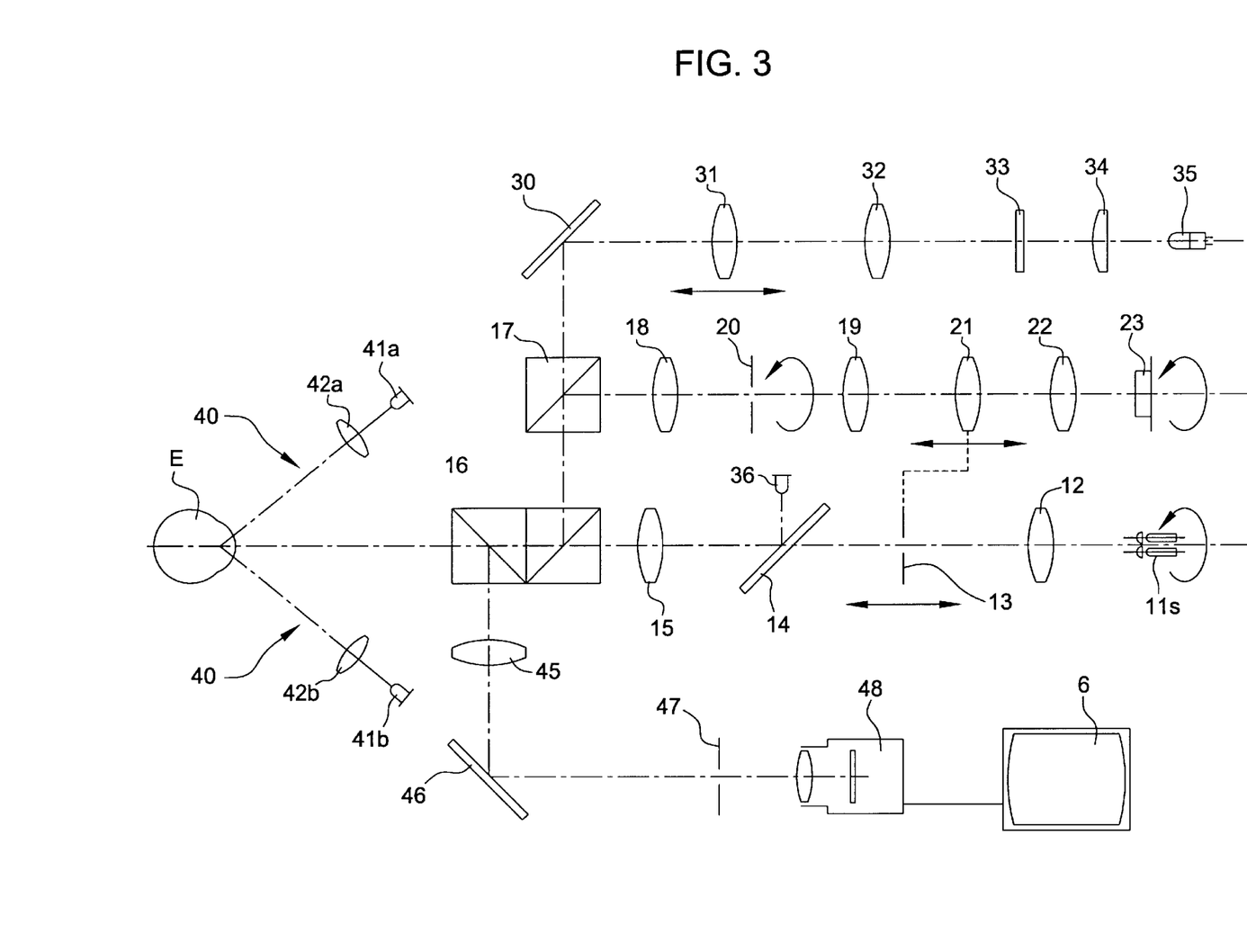
FIG. 3 is a view showing a outline arrangement of optical system of the preferred embodiment viewed from the upper angle of the present invention.

FIG. 3 is a view showing a outline arrangement of optical system of the preferred embodiment viewed from the upper angle. The detail of each optical system of the present apparatus such as a measurement optical system, a fixation target optical system, an alignment target optical system and an observation optical system will be described respectively herein.

(Measurement optical system)

Reference numeral 11s denote two light sources having a wavelength in an infrared region, and they are placed so as to enable to rotate around the optical axis. Reference numeral 12 is a condenser lens, thereby the light sources 11s are positioned at a front focal point of the condenser lens 12. Reference numeral 13 is a target plate for measurement which has a target for measurement (spot aperture), and the target plate 13 is movable to be placed at a conjugate position relative to a fundus of an eye E to be examined.

Reference numeral 14 is a beam splitter, which is coaxial with an optical axis of a first target projection optical system that will be described hereafter. Reference numeral 15 is a projection lens so as to project the target for measurement on the fundus of the eye. Reference numeral 16 and 17 are beam splitters. Reference numeral 18 and 19 are relay lenses, 20 is a belt-type corneal reflecting rejection mask which is placed at a conjugate position relative to a cornea of the eye E, 21 is a movable lens which is moved with the target plate 13, and 22 is an image-forming lens. Reference numeral 23 is a photodetector for measurement, and the photodetector 23 is rotated around the optical axis by synchronizing with the light sources 11s for measurement and the corneal reflecting rejection mask 20.

(Fixation target optical system)

Reference numeral 30 is a mirror, 31 is a first relay lens which is movable on the optical axis, thereby the eye is fogged by a movement of the first relay lens 31 on the optical axis. Reference numeral 32 is a second relay lens, 33 is a fixation target which is placed at a focal point of the second relay lens 32, 34 is a condenser lens, and 35 is a illumination lamp.

(Alignment target projection optical system)

An alignment target projection optical system is constituted by two target projection optical systems. They are a first target projection optical system for projecting a target from a visual axial direction, and a second target projection optical system having an optical axis with a predetermined angle opposite to the first target projection optical system.

The first target projection optical system has a following constitution. Reference numeral 36 is a point light source for emitting a light of infrared light, the point light source 36 is positioned at the front focal point of the projection lens 15 passed through the beam splitter 14. A luminous flux emitted from the point light source 36 is changed to be a parallel luminous flux by the projection lens 15, thereby an image of point light source is formed by corneal reflection of the eye E.

Figure 4:
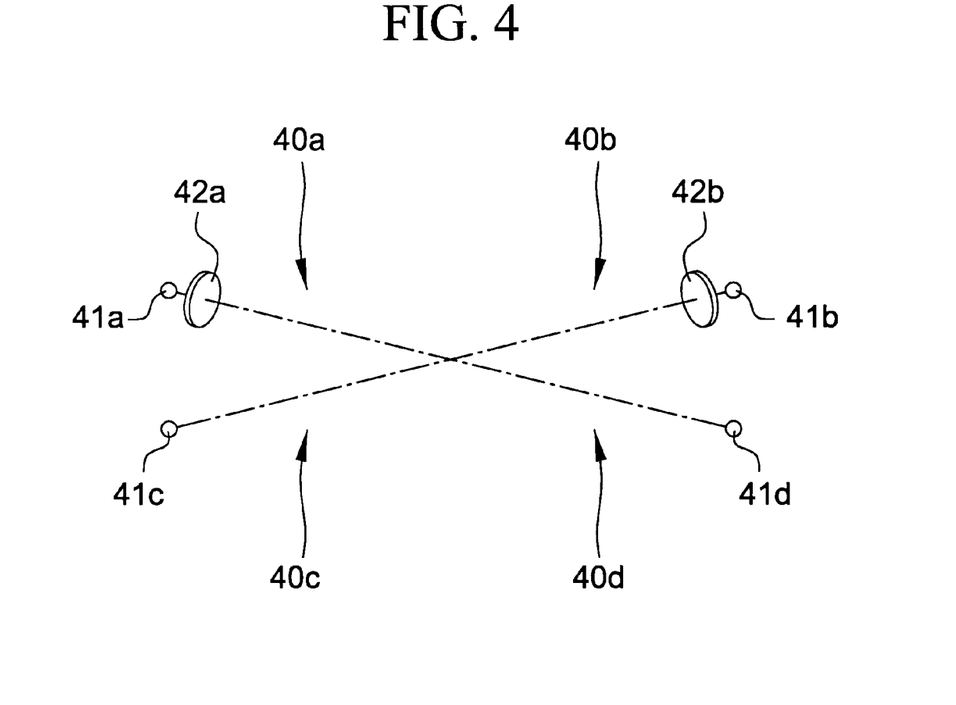
FIG. 4 is a view showing a second target projection optical system in FIG. 3 viewed from an examinee's side.

Reference numeral 40 is a second target projection optical system, wherein 4 pairs (40a–40d) of projection optical systems are placed so as to cross measurement optical axes in the center, also each projection optical system is placed with holding a predetermined angle opposite to the measurement optical axis. FIG. 4 is a view showing the second target projection optical system 40 viewed from an examinee's side. The projection optical systems 40a and 40b comprise the point light sources 41a and 41b for emitting the infrared light and collimating lenses 42a and 42b respectively, so that an infinite target is projected from upper angle opposite to the eye E. The projection optical systems 40c and 40d comprise the point light sources 41c and 41d for emitting the infrared light, so that a finite target is projected from lower angle opposite to the eye E. The image of corneal reflection is formed at the periphery of cornea of the eye by these projection optical systems 40a–40d. Consequently, a reflection light caused by the corneal reflection is not turned into a detecting range of the measurement optical system. Also without taking any measures to remove the reflection light at the cornea (or diaphragm may be disposed at a conjugate position with receiving light system), the influence on the measurement optical system can be avoided.

(Observation optical system/Alignment target detecting optical system)

After the luminous flux from an anterior part of an eye to be examined is reflected at the beam splitter 16, the luminous flux is photographed by a CCD camera 48 passed through an objective lens 45, a mirror 46 and a telecentric diaphragm 47. An anterior part image of the eye E, and the corneal reflection image of four light sources 41s and the light source 36 photographed by the CCD camera 48 are displayed on the TV monitor 6. Also, the alignment condition is detected depending on a position of the corneal reflection image photographed by the CCD camera 48.

Figure 5:
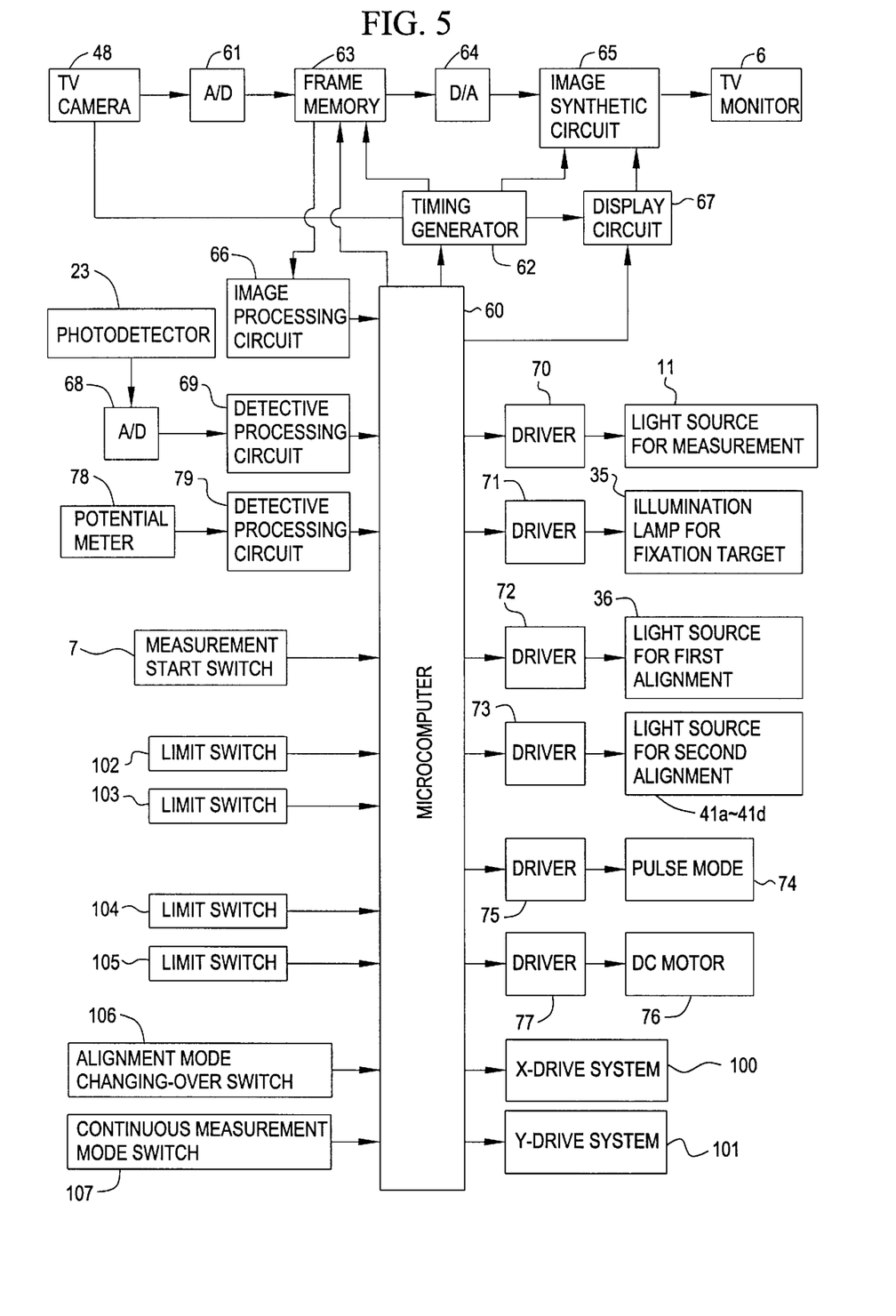
FIG. 5 is a view showing a detail constitution of control system of the apparatus.

FIG. 5 is a view showing a detail constitution of control system of the apparatus. A video signal from the CCD camera 48 is digitized by an A/D converter 61, thereby the video signal is taken into a frame memory 63 by synchronizing with a signal of a timing generator 62. An image taken into the frame memory 63 is displayed simultaneously on the TV monitor 6 passed through a D/A converter circuit 64 and an image synthetic circuit 65.

Reference numeral 66 is a image processing circuit for processing the image which is taken into the frame memory 63 so as to detect the alignment target image, and a microcomputer 60 controls so that a coordinate point of target image can be obtained by a signal from the image processing circuit 66.

Reference numeral 67 is a display circuit for producing reticle marks, graphics, characters information and the like in order to display on the TV monitor 6. The display circuit 67 has an IC chip for storing predetermined characters. A signal from the display circuit 67 is synthesized with a picture signal from the CCD camera 48 by the image synthetic circuit 65 so as to display on the TV monitor 6. Reference numeral 68 is an A/D converter. After a signal from the photodetector 23 is digitized by the A/D converter 68, a predetermined processing is carried out by a detective processing circuit 69 so as to input the signal into the microcomputer 60.

Reference numeral 70 is a driver for driving the light sources 11s for measurement, 71 is a driver for driving the illumination lamp 35 for fixation target, 72 is a driver for driving the light source 36, and 73 is a driver for driving the light sources 41a–41d. Reference numeral 74 is a pulse motor for rotating the light sources 11s for measurement, the corneal reflecting rejection mask 20 and the photodetector 23, and 75 is a driver for driving the pulse motor 74. Reference numeral 76 is a DC motor for moving the target plate 13 for measurement and the movable lens 21, and 77 is a driver for driving the DC motor 76. Reference numeral 78 is a potential meter for detecting a moved position of the target plate 13 for measurement, and 79 is a detective processing circuit for taking a predetermined processing for a signal from the potential meter 78.

Reference numeral 100 is a X-drive system for driving the measuring unit 4 in the left-right direction opposite to the body unit 3, which is constituted by such a slide mechanism, a motor or a driving circuit of motor and the like. Reference numeral 101 is a Y-drive system for driving the measuring unit 4 in the up-down direction opposite to the body unit 3, which is constituted of such a slide mechanism, a motor or a driving circuit of motor and the like.

Reference numerals 102 and 103 are limit switches for respectively detecting a limit of shifting of the left or right direction opposite to the body unit 3, and 104 and 105 are limit switches for respectively detecting a limit of shifting in the up direction or the down direction opposite to the body unit 3.

Reference numeral 106 is an alignment mode changing-over switch for selecting a manual alignment mode or an automatic alignment mode, and 107 is a continuous measurement mode switch for enabling a continuous measurement until a measured result reaches a predetermined number by starting automatic measurement.

Next, the operation method for the above-mentioned apparatus will be described herein. In this part, the case of selecting the automatic alignment mode will be explained.

Figure 6:
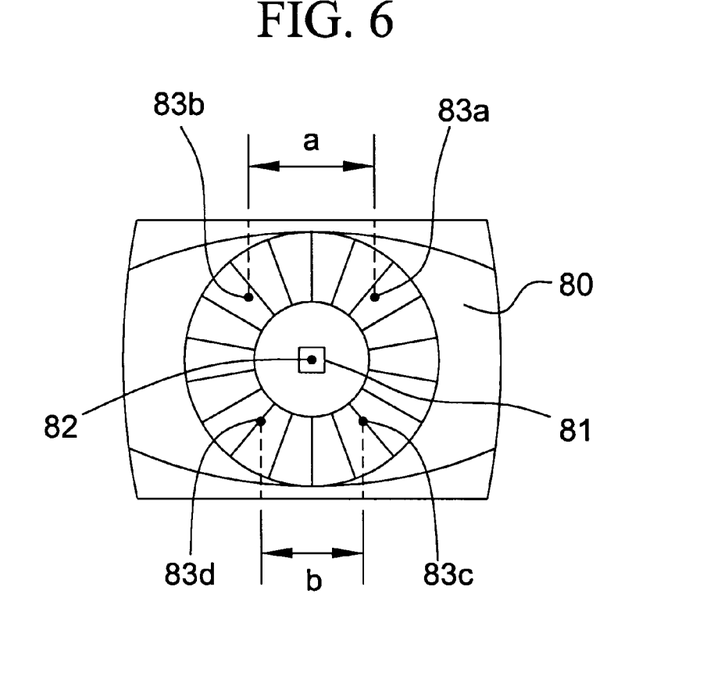
FIG. 6 is a view showing a screen sample upon alignment.

First, the operator adjusts a position of the examinee's face on the face support unit 2 so as to fix the eye to be examined. With observing a target image of corneal reflection or reticle mark displayed on the TV monitor 6, a rough alignment is performed by operating the joystick 5 or the like. FIG. 6 is a display sample upon the alignment. Reference numeral 80 is an image of anterior part of an eye, 81 is a reticle mark which is electrically formed by the display circuit 67 (reticle mark may be also formed optically). Reference numeral 82 is a target image of the light source 36 of the first target projection optical system which is formed by reflection in the center of cornea. Reference numeral 83a–83d are target images by corneal reflection of the point light sources 41a–41d of the second target projection optical system 40. By handling the joystick 5, the operator shifts the body 3 toward and away or left and right, also by handling the rotating knob 5a, the measuring unit 4 is shifted up and down opposite to the body unit 3, thereby an alignment adjustment is performed so that the target image 82 positioned around the center of the image 80 can be headed for the reticle mark 81 (the height of the chin support member 2a may be adjusted if necessary).

When five target images are caught by the CCD camera 48, the automatic alignment of XY directions is ready to be started. By the microcomputer 60, one target image 82 positioned in the center is extracted and processed from among five other targets images detected by a signal from the image processing circuit 66, and it is detected that alignment conditions of XY directions of the measuring unit 4 (measurement optical system) opposite to the eye to be examined. As a result, shifting distances of X and Y directions of the target image 82 from the optical axis are obtained respectively. Based on the information of the shifting distance, the X-drive system 100 and the Y-drive system 101 are driven by the microcomputer 60. When the measuring unit 4 is shifted by driving the X-drive system 100 and the Y-drive system 101, the target image 82 from the corneal center is moved on a photographic element of the CCD camera 48. Therefore, the shifting distance is obtained steadily by the microcomputer 60. The microcomputer 60 judges whether such an obtained shifting distance is within a predetermined allowable condition. After it is judged the shifting distance is within the predetermined allowable condition, the alignment of XY directions is completed by stopping operations of the X-drive system 100 and Y-drive system 101.

Figure 7A:
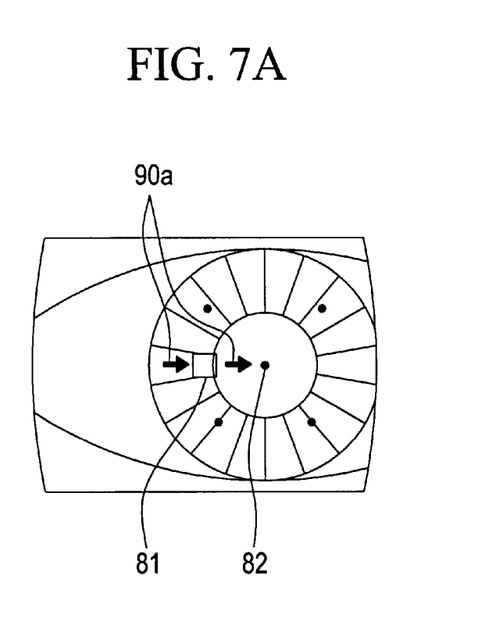
FIGS. 7A–7D are views showing display samples on a TV monitor of directional indicators that a body unit 3 or a chin support member 2a should be shifted.
Figure 7B:
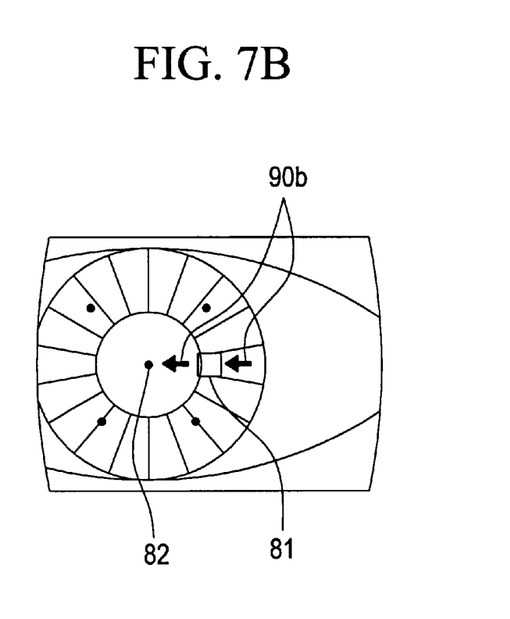
Figure 7C:
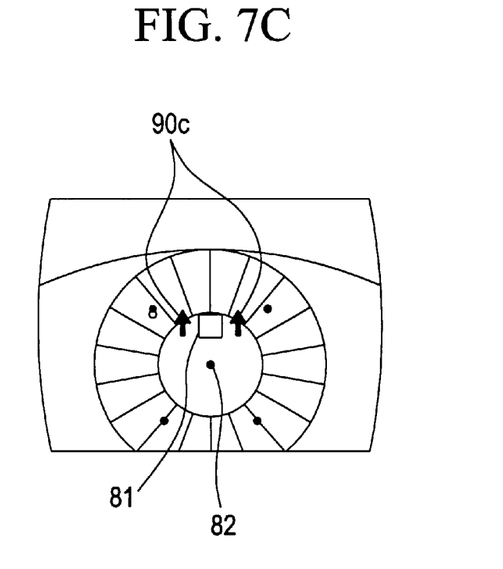
Figure 7D:
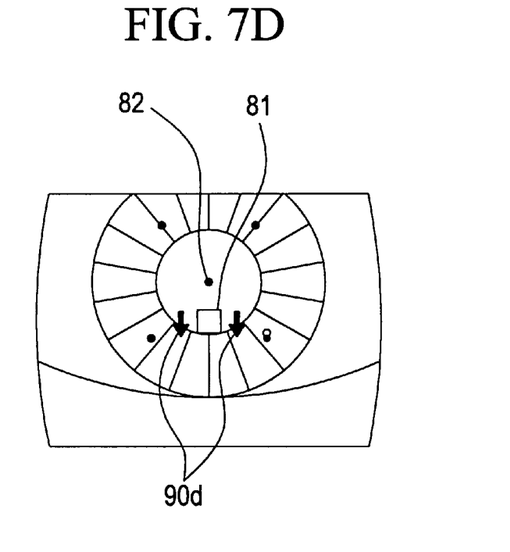

Under the condition that the target image 82 is not within the predetermined allowable condition upon completion of alignment, when it is detected by any limit switch 102–105 of XY directions that the shifting of measuring unit 4 is limited, by the microcomputer 60, a command is sent to the display circuit 67 based on an input of detecting signal so as to display indicators on the TV monitor 6 to inform the operator which direction the body unit 3 or the chin support member 2a should be moved. FIG. 7A is a display sample of a right limit viewed from the operator side, FIG. 7B is a display sample of a left limit, FIG. 7C is a display sample of a down limit, and FIG. 7D is a display sample of an up limit. It is displayed that a right-arrow indicator 90a, a left-arrow indicator 90b, an up-arrow indicator 90c and a down-arrow indicator 90d for indicating a moving direction are on both sides of the reticle mark 81. When the right-arrow or the left-arrow indicator is displayed, by handling the joystick 5, the body unit 3 needs to be shifted in a direction of which arrows are displayed opposite to the base 1, then the shifting limitation of the measuring unit 4 is canceled. When the up-arrow or the down-arrow indicator is displayed, by turning the knob 2b, the chin support member 2a needs to be shifted in a direction of which arrows are displayed, then the shifting limitation of the measuring unit 4 is canceled. As described above, since such a indicator for indicating a shifting direction is displayed near the reticle mark 81, the operator can concentrate on alignment without moving his line of sight. It is easy for the operator to notice a display of moving indication, also the operator can take necessary measures immediately. Further, because the indicators 90a–90d are predetermined characters which are stored in the IC chip, it may be possible to simplify a hardware setting or software setting of the apparatus, as well as to improve a display speed.

After the alignment of XY directions is completed by the automatic alignment, the operator handles the joystick 5 in order to shift the measuring unit 4 toward and away opposite to the eye to be examined, so that an alignment adjustment of working distance is performed. The apparatus provides means for judging the alignment condition of working distance by detecting the target image of the second target projection optical system.

The judging of the alignment condition of working distance will be described herein. The microcomputer 60 calculates respectively a distance between the target image 83a and 83b and a distance between the target image 83c and 83d which are processed and obtained by the image processing circuit 66. The target image 83a and 83b are images of light source which are placed optically at an infinite distance. Even though the apparatus deviates in the working-distance direction, the distance between the target image 83a and 83b is hardly changed. On the other hand, since the target image 83c and 83d are images of light source which are placed optically at a finite distance, its distance is changed depending on the displacement of the working distance of the apparatus (the detail of this relation is described in Japanese Patent Laid open No.6-46999 corresponding to U.S. Pat. No. 5,463,430).

By applying the characteristic of the above-mentioned relation, it is assumed that the distance between the target image 83a and 83b is "a", also the distance between the target image 83c and 83d is "b" so as to set a formula, b/a=S, for finding the working distance between the eye to be examined and the apparatus ("S" is a value having a set range by relation with alignment accuracy). Consequently, the alignment condition of the working distance can be detected as follows.

(A) b/a>S indicates that the eye to be examined deviates forward.

(B) b/a=S indicates that alignment of the working distance is completed.

(c) b/a<S indicates that the eye to be examined deviates backward.

Figure 8:
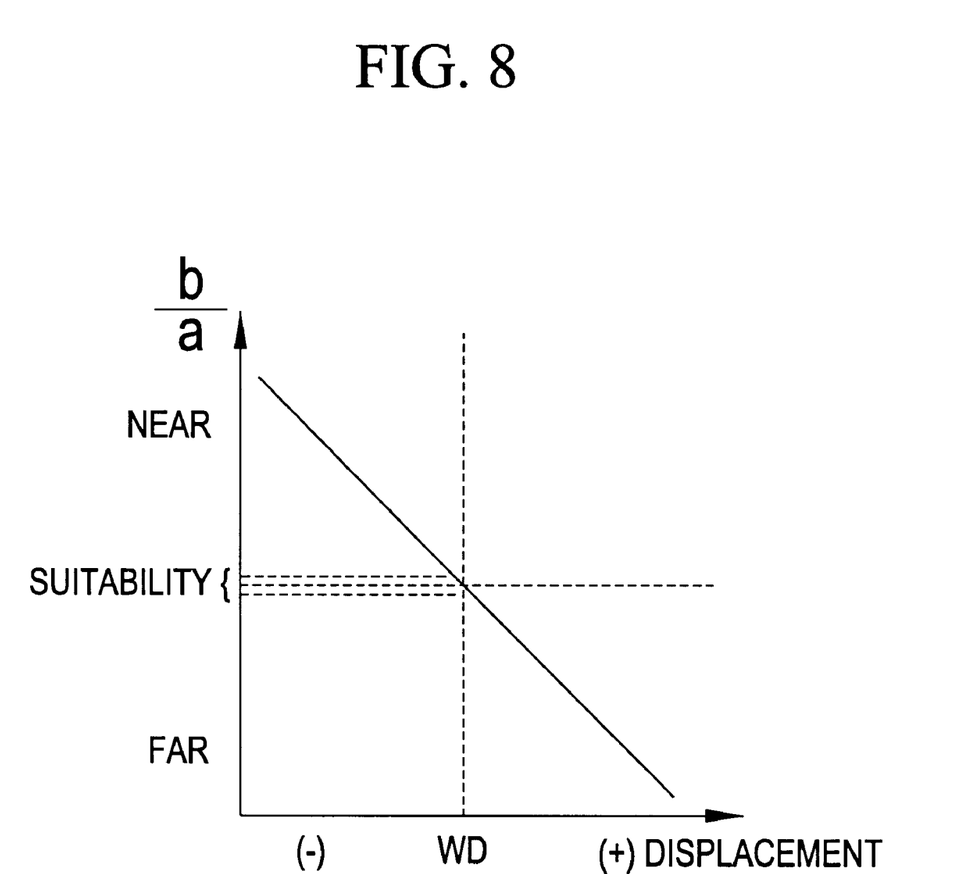
FIG. 8 is a view explaining a detecting of displacement of working distance.

Also, it is possible to know the displacement of the working distance by beforehand calculating information of relation to a value of "b/a" such as shown FIG. 8.

Figure 9A:
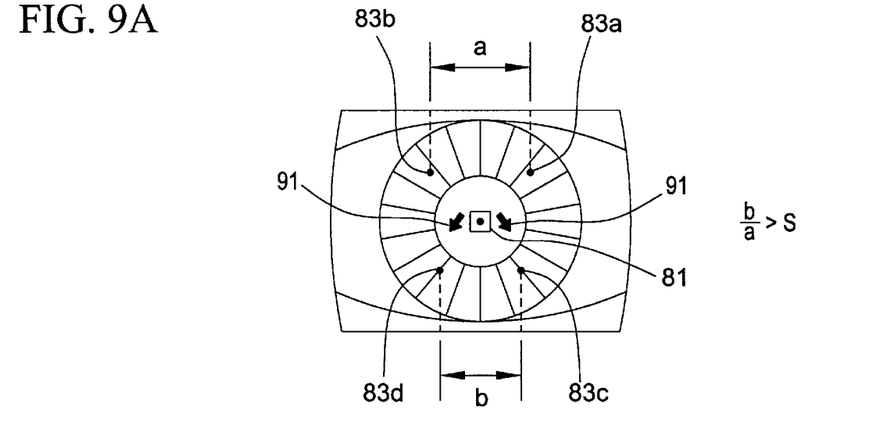
FIGS. 9A–9C are views showing display samples on a TV monitor of directional indicators that a measuring unit 4 should be moved at a working-distance direction.
Figure 9B:
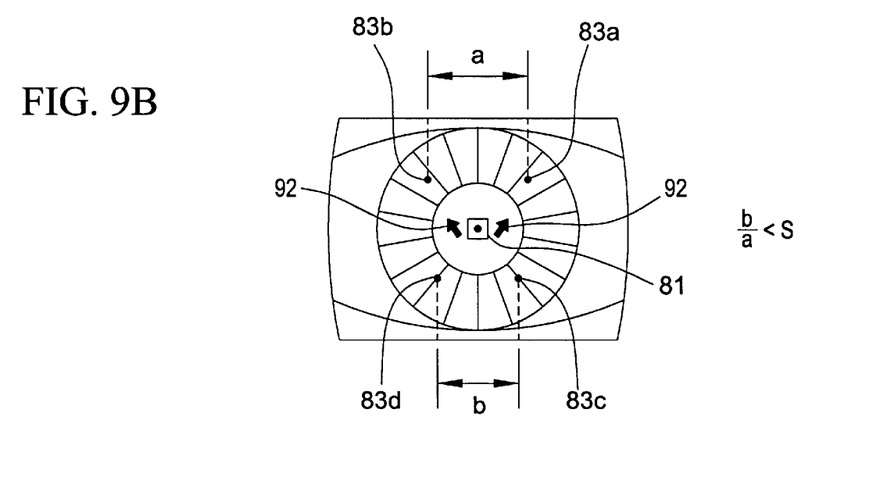
Figure 9C:
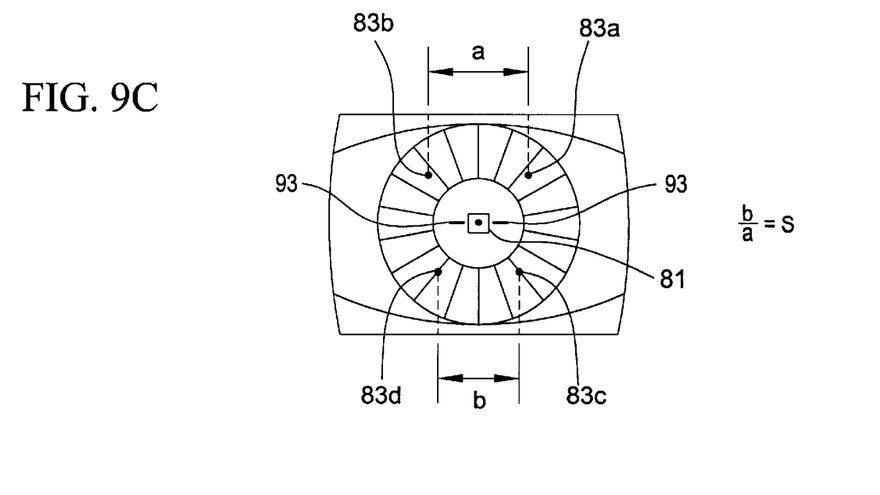

Based on information of the alignment condition of the working distance, a command is sent to the display circuit 67 by the microcomputer 60, so that indicators for informing the operator which direction the measuring unit 4 should be shifted are displayed on the TV monitor 6. FIGS. 9A–9C are display samples of directional indicators. FIG. 9A is a view when the eye to be examined deviates forward (b/a>S). Indicator arrows 91 for slantingly pointing down are displayed on both sides of the reticle mark 81, and this means that the body unit 3 and measuring unit 4 need to be shifted away from the eye to be examined. FIG. 9B is a view when the eye deviates backward (b/a<S). Indicator arrows 92 for slantingly pointing up are displayed on both sides of the reticle mark 81. This means that the measuring unit 4 needs to be shifted toward the eye to be examined (close to the eye). FIG. 9C is a view when the alignment of the working distance is completed (b/a=S). Indicator bars 93 are displayed on both side of the reticle mark 81. Indications of these indicators 91–93 are predetermined characters which are stored into the IC chip. Besides, modulation of sounds or programed tones may be also applied to inform the operator of the alignment adjustment of the working distance.

The operator follows such instructions of the alignment of the working distance, and shifts the body unit 3 toward and away by handling the joystick 5, so that the alignment adjustment of the working distance direction can be completed. The microcomputer 60 controls that a trigger signal is automatically generated based on a judged result of the alignment condition of the working-distance direction and the up-down/left-right directions under a predetermined condition, thereby a measurement (hereinafter, this is called Auto measurement) is started. A measurement luminous flux emitted from the light sources 11s for measurement is passed through the condenser lens 12, the target plate 13, the beam splitter 14, the projection lens 15 and the beam splitter 16 so as to be condensed at an adjacent to a cornea of the eye E, then the luminous flux reaches at the fundus of the eye. In case of a normal eye without ametropia, the target image reflected at the fundus is reflected at the beam splitter 17 and passed through the relay lenses 18 and 19, thereby the target image is formed on the photodetector 23 by the image-forming lens 22. In case of an eye with ametropia, based on the received signal of a reflection light at the fundus received by the photodetector 23, the microcomputer 60 drives the DC motor 76 for moving the movable lens 21 and the target plate 13 so as to be placed at a conjugate position relative to the fundus of the eye E.

Next, after the first relay lens 31 is moved so that the fixation target 33 and the fundus of the eye E are placed at a conjugate position, the relay lens 31 is further moved so as to be fogged only for a portion of appropriated diopter. Under the condition that the eye E is fogged, the light sources 11s for measurement, the corneal reflecting rejection mask 20 and the photodetector 23 are rotated 180 degree around the optical axis. During the rotation, the target plate 13 and the movable lens 21 are moved by the signal from the photodetector 23, so that the movement distance is detected by the potential meter 78 so as to find the refractive power value of each longitude direction. The microcomputer 60 calculates the refractive power of the eye to be examined by taking a predetermined processing for this refractive power value.

When the measurement is completed, based on a detection of target image by the first and second target projection optical systems, it is confirmed by the microcomputer 60 whether the condition is again under the predetermined alignment condition (this confirmation may be effective when an auto tracking for tracking a movement of the eye upon measurement is not performed). In case that any alignment condition of either up-down/left-right directions or working-distance direction deviates from a predetermined allowable condition, it is judged that the alignment displacement of the eye is caused upon measurement. Therefore, an obtained measured result is cancelled and an error indication is displayed on the TV monitor 6. The measurement should be started again when the error indication is displayed. The above-mentioned process may prevent from selecting such an improper measured result caused by alignment displacement after the measurement is started. Especially, in case of mechanism for starting the measurement by automatically generating the trigger signal, it may result in that the measurement happens to be started the instant alignment condition is completed without intention. However, the present ophthalmic apparatus can prevent from selecting such a less reliable measured result by mistake. Further, if a checking of the alignment displacement is performed upon measurement (especially just at starting an actual measurement), more reliable measured result can be obtained. In case that the measured result is proper by confirmation of alignment condition after the measurement is completed, measured result is displayed on the TV monitor 6.

Besides, regarding confirmation of the alignment condition after the measurement is completed (or when the actual measurement is started), the alignment displacement of the working-distance direction is informed as shown in FIG. 8. Therefore, the measured result may be corrected based on the displacement. In this case, the correction is described as follows. Assuming a refractive power value which is obtained by the measurement is "Dx" (diopter), a displacement of working distance from a proper position when the measurement is completed is "x" (mm), and a focal distance of a actual refractive power degree of the eye at a proper working distance is "F" (mm), the following formula is described;

$$1000/(F+x)=Dx$$

a value of "F", focal distance, is found out by the above-mentioned formula, thereby a corrected refractive power value can be obtained by converting the value of "F" to refractive power.

In case of the continuous measurement mode for performing a plural measurement for the same eye to be examined, the Auto measurement is performed successively. If there is not any alignment displacement by applying a confirmed result of the alignment displacement upon the previous measurement, it may be possible to carry out next measurement. Such a continuous Auto measurement is kept performing until measured results of predetermined times (for instance, 3 times) which is set beforehand are obtained. In this case, an average value and a standard deviation of plural measured results are calculated so as to exclude measured results which the standard deviation deviates from a predetermined value. In addition, if further measurement is continued, more reliable and accurate measured result can be obtained. When the measured results of the predetermined times are obtained, the trigger signal is stopped generating by the microcomputer 60, also the Auto measurement is not performed even under the condition that alignment is completed.

After the trigger signal is stopped generating, the apparatus still continues to detect alignment target, and it is monitored by the apparatus whether target image is not detected continuously for the duration of a predetermined period (for example, for 1 second). In case that the target image is not detected continuously for the duration of the predetermined period (not at a temporary period), this means that the eye has been taken away from a fixed position, or one eye has been changed to the other eye. Therefore, it is regarded that measurement have been completed. The apparatus is restored to its condition that the trigger signal can be generated again (it is cancelled that the trigger signal is stopped generating). By the above-mentioned process, even though another measurement of the same eye has to be repeated again after the measured results of the predetermined times are obtained, once the eye is kept space away from the measuring unit 4 so as to start alignment again. Consequently, without operating measuring start switch 7, such a continuous Auto measurement can be possible. Since it is not necessary for the mode of the Auto measurement that the measuring start switch 7 is pressed constantly, the operator can concentrate on the measurement. In addition, because the measurement can be resumed without using the measuring start switch 7, electric troubles caused by wires of the measuring start switch 7 (another trouble of break which is caused by wiring inside such a mobile joystick) can be avoided. Further, if the apparatus is not equipped with the measuring start switch 7, production cost of the apparatus can be reduced.

Regarding predetermined period for monitoring whether the target image is not detected continuously, if the predetermined period are spaced more than a period of moments blinking of an eye or moving of line of sight, it is possible to avoid that unnecessary Auto measurement is resumed due to these intentions.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus having measuring means for measuring an eye to be examined, the ophthalmic apparatus comprising:

alignment detecting means for detecting an alignment condition of said measuring means corresponding to the eye to be examined;

alignment judging means for judging whether the alignment condition is possible to measure based on a detected result by said alignment detecting means;

trigger signal generating means for generating a trigger signal for starting measurement; and measured result judging means for judging that a measured result is error when said alignment judging means judges that the alignment condition after starting measurement deviates from a predetermined allowable standard based on the detected result by said alignment detecting means during measurement or when measurement is completed.

2. The ophthalmic apparatus according to claim 1, wherein said trigger signal generating means including control means for controlling to generate the trigger signal for starting measurement based on the judged result by said alignment judging means.

3. The ophthalmic apparatus according to claim 1, further comprising informing means for informing an operator of the judged result by said measured result judging means.

4. The ophthalmic apparatus according to claim 1, wherein said alignment detecting means having first alignment detecting means for detecting the alignment condition of up-down/left-right directions of said measuring means corresponding to the eye to be examined, and second alignment detecting means for detecting the alignment condition of a working-distance direction of said measuring means corresponding to the eye to be examined.

5. The ophthalmic apparatus according to claim 4, further comprising correcting means for correcting the measured result based on a displacement of working distance which is obtained on the basis of the detected result by said second alignment detecting means.

6. An ophthalmic apparatus having measuring means for measuring an eye to be examined, the ophthalmic apparatus comprising:

target projecting means for projecting an alignment target onto the eye to be examined;

target detecting means for detecting a target image formed by said target projecting means;

alignment judging means for judging whether an alignment condition is possible to measure based on a detected result by said target detecting means;

trigger signal generating-controlling means for generating a trigger signal for starting measurement based on a judged result by said alignment judging means;

stop means for stopping said trigger signal from being generated whenever a desired measured result is obtained;

monitoring means for monitoring whether said target image is detected within a predetermined period by said target detecting means when said trigger signal is stopped from being generated by said stop means; and cancel means for cancelling a stop of generation of the trigger signal when said monitoring means monitors that the target image is not detected within the predetermined period by said target detecting means.

7. The ophthalmic apparatus according to claim 6, further comprising measured result judging means for judging that a measured result is error when said alignment judging means judges that the alignment condition after starting measurement deviates from a predetermined allowable standard based on the detected result by said target detecting means during measurement or when measurement is completed.

8. The ophthalmic apparatus according to claim 6, wherein the predetermined period for monitoring is spaced longer than periods of blinking of the eye and moment moving of line of sight.

9. The ophthalmic apparatus according to claim 6, further comprising:

photographing means for photographing an anterior part of the eye to be examined;

display means for displaying a photographed image by said photographing means; and reticle forming means for forming a reticle mark for alignment on a display screen of said displaying means.

10. The ophthalmic apparatus according to claim 6, further comprising measurement control means for continuously controlling to execute a plural measurement.

11. The ophthalmic apparatus according to claim 6, further comprising:

measurement control means for continuously controlling to execute a plural measurement; and measured result judging means for judging that the measured result is error when said alignment judging means judges that the alignment condition after starting measurement deviates from the predetermined allowable standard based on the detected result by said target detecting means during measurement or when measurement is completed, wherein the desired measured result which is an operating condition of said stop means is a effective measured result of set numbers.

* * * * *